US00PP34451P2

(12) United States Plant Patent
Smit

(10) Patent No.: US PP34,451 P2
(45) Date of Patent: Jul. 26, 2022

(54) ***PEPEROMIA* PLANT 'EC-PEPE2112'**

(50) Latin Name: *Peperomia caperata*
Varietal Denomination: 'EC-PEPE-2112'

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/679,224

(22) Filed: Feb. 24, 2022

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Peperomia* plant named 'EC-PEPE-2112' is disclosed, characterized by round, light green leaves with a puckered surface, and deep-lying veins. Plants have compact, rosette-like habits. The new variety is a *Peperomia*, typically used as an ornamental plant.

3 Drawing Sheets

Latin name of the genus and species: *Peperomia caperata.*

Variety denomination: 'EC-PEPE-2112'.

BACKGROUND OF THE INVENTION

The new cultivar is a product of a planned breeding program to produce distinct and better performing *Peperomia* varieties. The new variety was selected as a seedling resulting from the crossing of *Peperomia caperata* 'A', and 'B', two unpatented varieties from the inventor's breeding line. The crossing was made by the inventor, Obed J. Smit, a citizen of the Netherlands in March 2018. 'EC-PEPE-2112' was selected by the inventor in the Fall of 2018 at a commercial greenhouse in Sappemeer, the Netherlands.

Asexual reproduction of the new cultivar 'EC-PEPE-2112' by terminal cuttings was first performed in Sappemeer, the Netherlands at a commercial greenhouse in September 2019, and has shown that the unique features of this cultivar are stable and reproduced true to type through successive generations.

SUMMARY OF THE INVENTION

The cultivar 'EC-PEPE-2112' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2112'. These characteristics in combination distinguish 'EC-PEPE-2112' as a new and distinct *Peperomia* cultivar:

1. Puckered leaf surface.
2. Deep-lying veins.
3. Small, round, light green leaves.
4. Compact, rosette-like habit.

PARENT COMPARISON

Plants of the new cultivar 'EC-PEPE-2112' are similar to plants of the female parent, *Peperomia caperata* 'A' in most horticultural characteristics, however, plants of the new cultivar 'EC-PEPE-2112' differ from in the following characteristics:

1. Leaves of the new variety are smaller than leaves of the seed parent.
2. Leaves of the new variety are light green on the upper side, while leaves of the seed parent are green on the upper side.

Plants of the new cultivar 'EC-PEPE-2112' are similar to plants of the male parent, *Peperomia caperata* 'B' in most horticultural characteristics, however, plants of the new cultivar 'EC-PEPE-2112' differ in the following characteristics:

1. Leaves of the new variety are light green on the upper side, while leaves of the seed parent are dark green on the upper side.

COMMERCIAL COMPARISON

Plants of the new cultivar 'EC-PEPE-2112' are similar to plants of the commercial variety *Peperomia* 'Burbella', U.S. Plant Pat. No. 32,564. However, plants of the new cultivar differ in the following characteristics:

1. Leaf upper side of the new variety is light green., while the leaf upper side of this comparator is grey.
2. Leaves of the new variety are smaller than leaves of this comparator.

Plants of the new cultivar 'EC-PEPE-2112' are similar to plants of the commercial variety *Peperomia* 'Schumi Red', unpatented. However, plants of the new cultivar differ in the following characteristics:

1. Leaves of the new variety are round, while leaves of this comparator are oblong with a pointed tip.
2. Leaf upper side of the new variety is light green, while leaf of this comparator is evenly red.
3. Leaves of the new variety are more puckered with deeper-lying veins than leaves of this comparator.

BRIEF DESCRIPTION OF THE PHOTOGRAPHS

The accompanying photograph in FIG. 1 illustrates in full color a typical blooming plant of 'EC-PEPE-2112' grown in a greenhouse. The plant is approximately 35 weeks of age.

Figure 1:
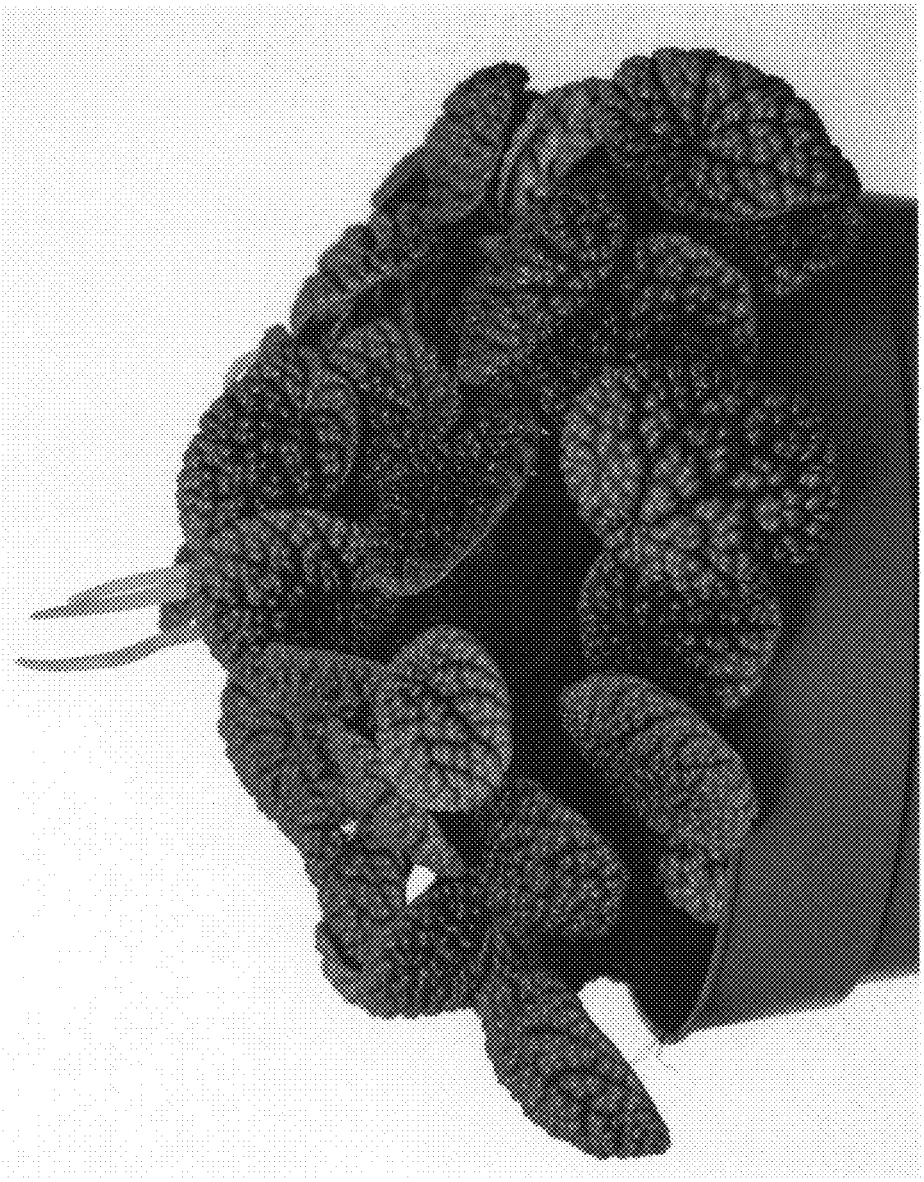
Figure 2:
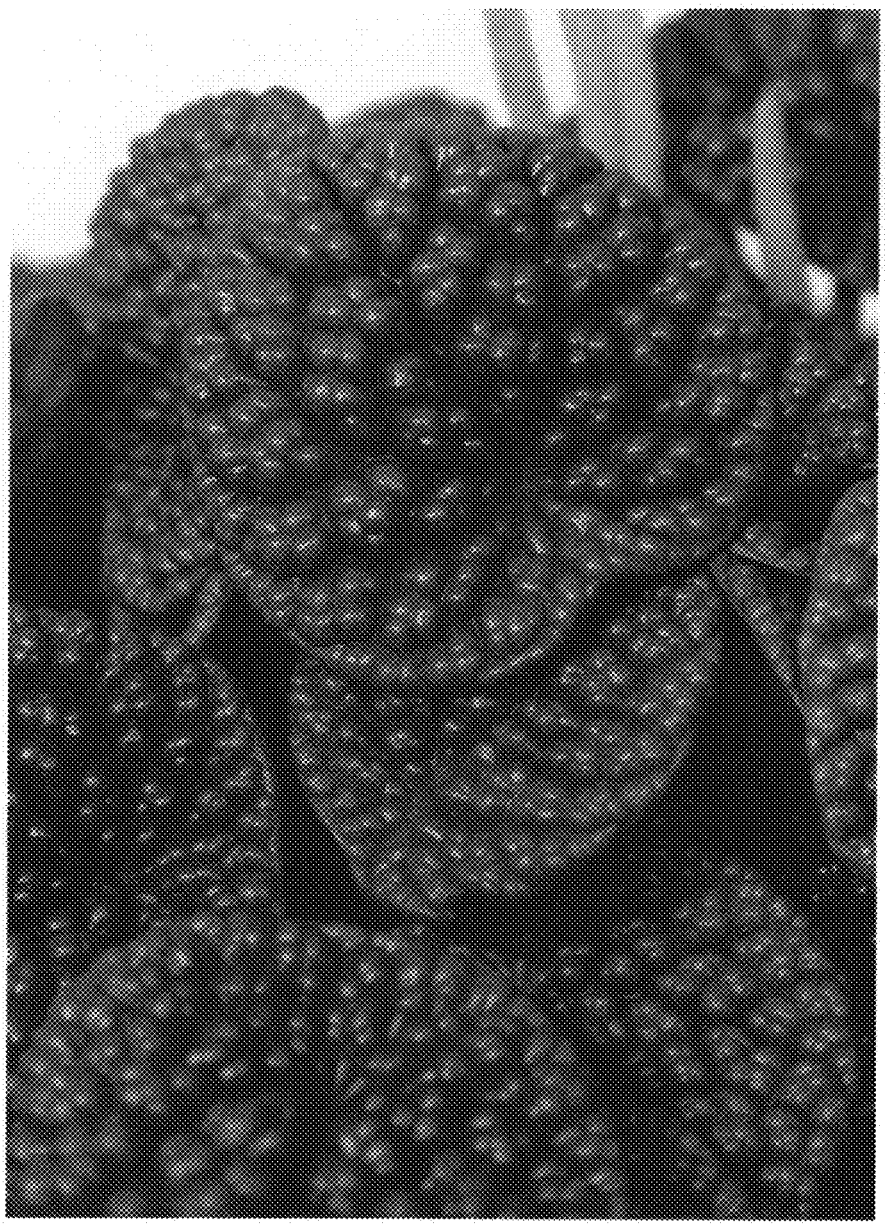
FIG. 2 illustrates a close up of the foliage.
Figure 3:
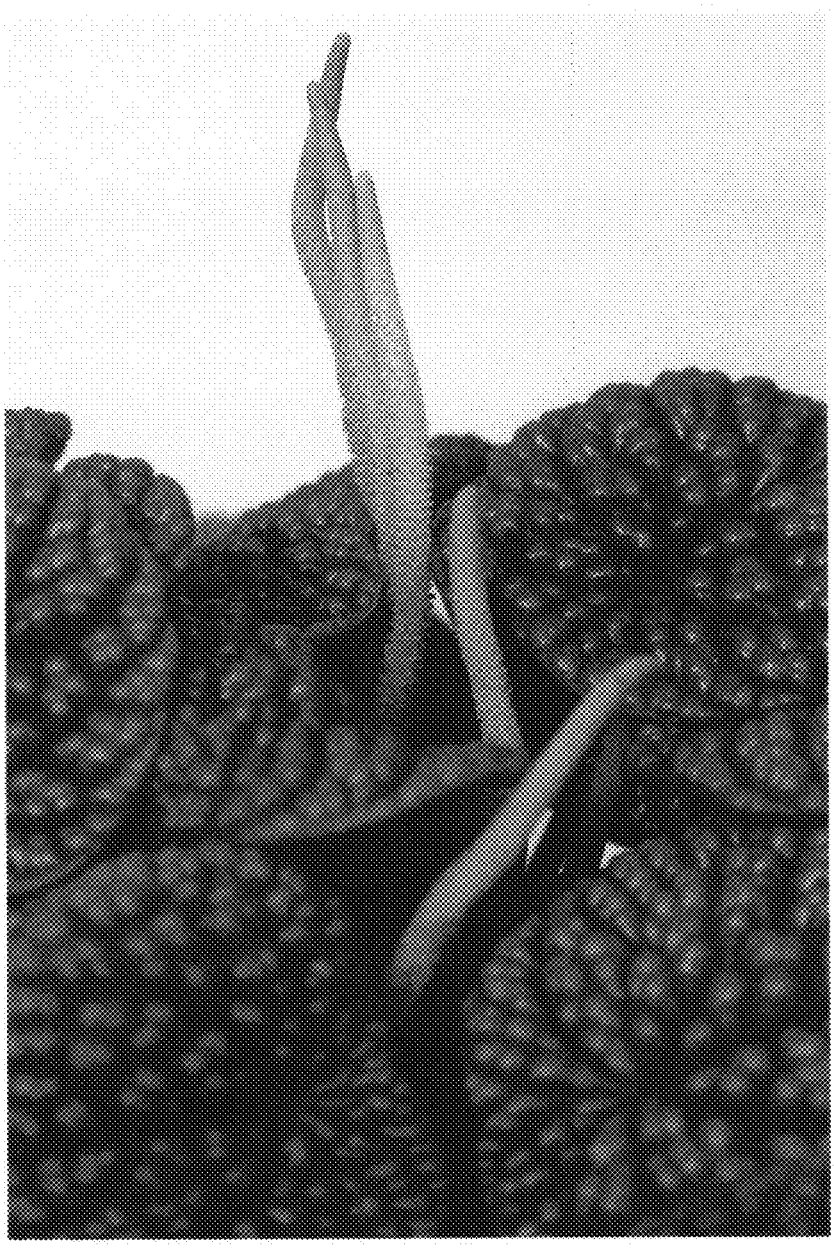
FIG. 3 illustrates a close up of inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2112' plants at 35 weeks of age, grown in a greenhouse in Sappemeer, the Netherlands during October. The growing temperature ranged from 18° C. to 20° C. at night to 20° C. to 22° C. during the day. Measurements and numerical values represent averages of typical flowering types.

Botanical classification: *Peperomia caperata* 'EC-PEPE-2112'.

PROPAGATION

Time to initiate roots: About 21 days at approximately 21° C. in summer.

Time to produce rooted cutting: About 28 days at 21° C. in summer.

Description of roots: Fibrous, fine, moderately dense, freely branching. White in color, not accurately measured with R.H.S. chart.

PLANT

Plant type: Perennial potted plant.

Plant shape: Flattened globular with inflorescences carried slightly above foliar plane.

Growth habit: Rosettes of leaves, eventually forming very short, thick stems.

Plant spread: Approximately 20.6 cm.

Height: 10.3 cm to top of foliar plane; 13 cm to top of floral plane.

Growth rate: Moderate.

Plant vigor: Moderate.

Age of plant described: Approximately 8 months.

Branching habit: Leaves in rosettes, eventually forming very short, thick stems, branching into lateral rosettes of leaves.

Pinching: Pinching not required.

Number of primary (main) branches per plant: Average 6.

Number of secondary (lateral) branches per plant: Average 2.

Main branches:

*Length*.—Average: 1 cm.

*Diameter*.—Average: 0.5 cm.

Internode length: Average: Less than 0.1 cm.

Appearance and shape: Succulent, thick and rounded.

Luster: Matte.

Aspect/angle from vertical: Average angle: 20°.

Strength: Moderately strong.

Color:

*Developing*.—RHS Yellow-Green 146D.

*Mature*.—RHS Yellow-Green 146D.

*At internodes*.—RHS Yellow-Green 146D.

Pubescence: None.

Plant fragrance: None.

FOLIAGE

Leaf:

*Arrangement*.—Alternate, single.

*Quantity*.—Average 8.

*Average length*.—4.4 cm.

*Average width*.—4.3 cm.

*Shape of blade*.—Near orbicular, perfoliate.

*Apex*.—Obtuse to rounded.

*Base*.—Truncate to obtuse, lobes connected and forming a perfoliate leaf.

*Margin*.—Entire, slightly revolute.

*Texture of top surface*.—Glabrous, smooth, moderately leathery, strongly bullate.

*Texture of bottom surface*.—Glabrous, smooth, moderately leathery.

*Pubescence*.—None.

*Luster, upper side*.—Glossy.

*Luster, under side*.—Matte, velvety.

*Color*.—Young foliage upper side: RHS Yellow-Green 144A, area surrounding veins slightly tinged Greyed-Orange 174A. Young foliage under side: RHS Yellow-Green 147D, veined 148B and 148C. Mature foliage upper side: RHS Green 137A, area surrounding veins Green 139A to Yellow-Green 147A, but darker. Mature foliage under side: RHS Greyed-Green 193A.

*Venation*.—Pattern: Parallel, strongly furrowed. Venation color upper side: RHS Green 139A to Yellow-Green 147A, but darker. Venation color under side: RHS Yellow-Green 148B.

*Petiole*.—Average Length: 7.3 cm. Diameter: 0.3 cm. Texture: Glabrous, smooth. Luster: Both sides very slightly glossy. Strength: Low. Color, upper side: RHS Yellow-Green N148C, moderately finely-striped Greyed-Red 182A, slightly more densely toward distal end. Color, under side: RHS Yellow-Green N148C, moderately finely-striped Greyed-Red 182A, slightly more densely toward distal end.

FLOWER

Inflorescence:

*Arrangement*.—Axillary spike.

*Inflorescence type and form*.—Spike.

*Inflorescence height*.—Average: 6.5 cm (excluding peduncle).

*Inflorescence diameter*.—Average: 0.3 cm.

*Quantity of flowers per inflorescence*.—Average 1,700 individual flowers per spike.

*Quantity of flowers per plant*.—Average 5,000.

*Quantity of flower buds per plant*.—Average 25,000.

*Quantity of flowers and buds per plant*.—Average 30,000.

*Natural flowering season*.—Fall into late spring.

Flower bud:

*Flower bud length*.—0.2 mm.

*Flower bud diameter*.—0.2 mm.

*Flower bud shape*.—Flattened, circular.

*Flower bud texture*.—Glabrous, smooth, slightly velvety.

*Flower bud luster*.—Slightly glossy.

*Flower bud color*.—Near RHS Yellow-Green 147C, tinged near Greyed-Purple 185C.

Flower:

*Flower type and form*.—Individual flowers are very small and consist of 1 bract, 2 stamens and a single pistil.

*Flower aspect*.—Outward.

*Flowering habit*.—Very freely.

*Fragrance*.—None.

*Flower shape*.—Rotate, consisting of 1 bract, 2 stamens and 1 pistil only; no petals and sepals present.

*Flower height*.—Average: 1 mm.

*Flower diameter*.—Average: 0.6 mm.

*Flower length*.—Average: 0.5 mm.

*Flower longevity on plant*.—Average one month.

*Persistent of self-cleaning?*.—Self-cleaning.

Peduncles:

*Terminal peduncle length*.—Average 6 cm.

*Terminal peduncle diameter*.—Average 2 mm.

*Peduncle angle to lateral branch axis*.—Average angle 30°.

*Peduncle strength*.—Weak.

*Peduncle texture*.—Glabrous, smooth.

*Peduncle luster*.—Moderately glossy.

*Peduncle color*.—RHS Yellow-green 148D, slightly finely-striped Greyed-Purple 185D.

Floral bracts:

*Quantity per flower*.—One below each individual flower.

*Shape*.—Orbicular.

*Length*.—0.4 mm.

*Width*.—0.4 mm.

*Color*.—Near RHS Yellow-Green 148c and 148D, slightly tinged near Greyed-Purple 185C.

REPRODUCTIVE ORGANS

Stamens:

*Number*.—Average 2.

*Filament length*.—Average 0.2 mm.

*Filament color*.—Near RHS Yellow-Green 146D.

Anther:

*Shape*.—Ovate.

*Length*.—Average 0.2 mm.

*Width*.—Average 0.15 mm.

*Color*.—Near RHS Greyed-Green 194D or lighter.

*Pollen*.—Low.

*Pollen color*.—RHS White 155A.

*Pistil*.—Number: Average 1. Length: Average 0.5 mm.

*Stigma*.—Shape: Flattened, hairy, circular. Length: Average 0.1 mm. Diameter: Average 0.2 mm. Color: Near RHS Yellow-Green 148D. Style: Sessile. Ovary color: Near RHS Yellow-Green 146D.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12. Moderate tolerance to rain. High tolerance to wind.

What is claimed is:

1. A new and distinct cultivar of *Peperomia* plant named 'EC-PEPE-2112' as herein illustrated and described.

* * * * *